United States Patent [19]

Lee et al.

[11] 4,054,137
[45] Oct. 18, 1977

[54] IRRIGATOR FOR BODY CAVITIES

[76] Inventors: Seung Joon Lee, 4703 Hickory Ave.; Leon Schreiner, 1603 E. 19th St., both of Cheyenne, Wyo. 82001

[21] Appl. No.: 702,215

[22] Filed: July 2, 1976

[51] Int. Cl.² .................................................. A61M 1/00
[52] U.S. Cl. ................................................... 128/234
[58] Field of Search ............... 128/234, 231, 230, 240, 128/251, 278, 214 B, 248

[56] References Cited

U.S. PATENT DOCUMENTS

| 2,093,344 | 9/1937 | Wandel | 128/214 B |
|---|---|---|---|
| 2,496,559 | 2/1950 | Piechaczek | 128/214 B |
| 3,098,480 | 7/1963 | Worthington | 128/214 B |
| 3,450,134 | 6/1969 | Willgerodt | 128/214 B |
| 3,860,000 | 1/1975 | Wooten et al. | 128/230 |
| 3,885,567 | 5/1975 | Ross | 128/278 |

FOREIGN PATENT DOCUMENTS 279,033  6/1969  Austria ..................... 128/214 B Primary Examiner—John D. Yasko
Attorney, Agent, or Firm—Ralph F. Crandell

[57] ABSTRACT

An irrigator for applying an irrigating solution to internal body cavities. A housing defines a first chamber for holding a supply of irrigating solution liquid for irrigating a body cavity and a second chamber for receiving waste liquid from the body cavity. A first single action pump in the housing receives a measured quantity of liquid from the first chamber and pumps the same into the body cavity. A second single action pump in the housing withdraws waste liquid from the body cavity and discharges the liquid into the second chamber. The first and second pumps are of the piston and diaphragm type, and each is provided with a port in communication with a single common conduit connectable with the body cavity.

7 Claims, 6 Drawing Figures

IRRIGATOR FOR BODY CAVITIES

FIELD OF THE INVENTION

The present invention relates to irrigators for body cavities and more specifically to an irrigator device for injecting irrigating liquid into body cavities and withdrawing liquid therefrom.

BACKGROUND OF THE INVENTION

It is conventional medical practice to irrigate body cavities with irrigating solution by using a large syringe. The syringe is first filled with an appropriate irrigating solution which is injected into the cavity and then withdrawn into the same syringe. The syringe is disconnected and the waste liquid discharged into a suitable container. Problems are created in that the syringe must be connected and disconnected to a tube leading to the body cavity for each irrigation. A variety of irrigating devices are shown in the art. See, for example, U.S. Pat. No. 3,398,743, issued Aug. 27, 1968, to S. Shalit, for "Closed System Irrigating Apparatus for Viscus Organs;" U.S. Pat. No. 295,755, issued Mar. 25, 1884, to J. A. Hawley, for "Vaginal Syringe;" and U.S. Pat. No. 13,975, issued Dec. 25, 1855, to J. Buhler, for "Syringe."

OBJECTS OF THE INVENTION

The principal object of the present invention is to provide an improved irrigating device for irrigating body cavities.

Another object of the present invention is to provide an irrigating device for body cavities which is simple in construction, compact, light weight, leak proof, easy to use and disposable.

A further object of the present invention is to provide an irrigator device of the foregoing character which can be used for a variety of irrigating solutions and which retains in a neat and clean manner both the irrigating solution and the waste solution for subsequent disposal.

SUMMARY OF THE INVENTION

Figure 1:
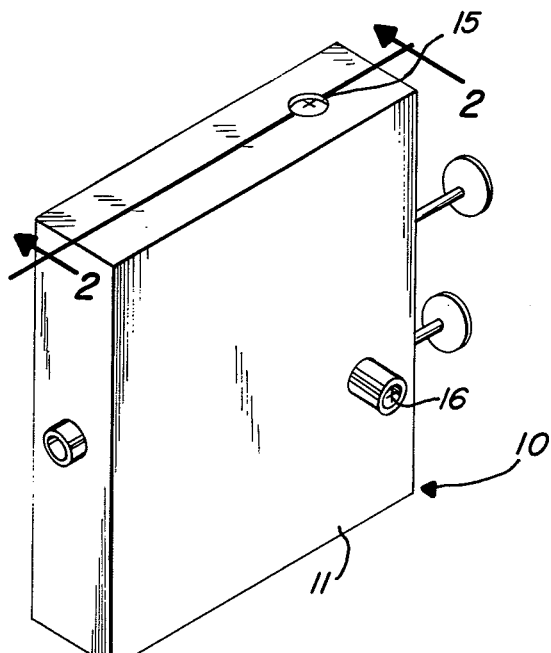
FIG. 1 is an isometric view of an irrigating device embodying the present invention.

In accordance with the foregoing objects, the present invention contemplates a unitary housing defining an upper or first chamber for holding a supply of an irrigating solution liquid for use in irrigating a body cavity and a second or lower chamber or waste chamber for receiving waste liquid from the body cavity. The chambers communicate with the body cavity through appropriate pumps and a single conduit. For pumping a measured amount of irrigating solution from the first or solution chamber into the body cavity, a first single action piston pump is provided in the housing. A second single action piston pump is likewise provided for use in withdrawing solution from the body cavity and discharging it into the waste receiving chamber. The pumps are generally similar in construction and each comprises a cylinder containing a sliding piston. The pistons are generally annular in shape and are provided with a central open spider portion to permit the passage of liquid through the piston. For preventing the flow of liquid through the pistons when the same are utilized for injecting fluid or discharging fluid from the body cavity, the pistons are formed with a diaphragm secured to the piston rods which covers and seals the central open portion of the piston. To this end, the first or injection pump includes a piston defining a central spider slidably supporting a piston rod. At the end of the rod, there is provided a boss for pulling the piston when the piston rod is pulled. On the opposite side of the piston, the rod is provided with a diaphragm seal so that when the piston rod is pushed, the piston is effectively sealed and forces solution into the body cavity.

In a similar manner, the discharge piston is formed by a central spider slidably supporting a piston rod with a diaphragm on the end of the rod which seats against the piston to provide a suction as the piston rod is pulled for withdrawing solution from the body cavity. On the opposite side of the piston, the rod is provided with a boss for pushing on the piston and at the same time allowing liquid to flow through the piston when the piston rod is pushed.

In operation, an irrigating solution is placed in the upper chamber and communicates through an appropriate port with the first piston pump. By pulling on the piston pump, the cylinder is filled with an irrigating solution. When filled, the user pushes on the piston rod and thereby forces irrigating solution into the body cavity. After an appropriate period of time, the user pulls on the discharge pump, which creates a slight vacuum sufficient to pull the fluid from the body cavity. After fluid has been discharged, the user pushes on the waste piston and thereby permits the discharged fluid to drain into the waste chamber.

The irrigator is a unitary compact device which is light in weight and well adapted for disposable applications. All fluids are fully contained within the unit, thereby providing for use under sanitary surrounding conditions. The unit is easy to use, light in weight, simple and inexpensive construction and is adapted to be disposable at a nominal cost.

DESCRIPTION OF THE INVENTION

Referring to the drawing, the irrigator device embodying the present invention is a self-contained, integral unit 10 formed by a housing 11 defining an upper chamber 12 for holding a supply of an irrigating solution liquid for irrigating a body cavity, and a lower or second chamber 14 for receiving waste liquid from the body cavity. For filling the upper first chamber 12, the housing 11 is provided with a filling port 15. For discharging or removing fluid from the second or waste chamber, the housing 11 is provided with an exhaust passage 16. The unit is desirably molded from a lightweight, inexpensive, disposable plastic material.

For injecting irrigating fluid into a body cavity and for withdrawing the waste fluids therefrom, the irrigator housing is provided with an integrally contained juxtaposed pair of pumps 18, 19 in communication with a single conduit or port member 20 defining a passage 21 adapted for connection with the body cavity through an appropriate flexible hose or conduit (not shown). In the embodiment shown, the pumps 18 and 19 are of the piston and cylinder type. To this end, the housing includes a first or upper cylinder 22 forming one wall portion of the first or upper chamber 12 and a second or lower cylinder 24 forming a portion of the wall of the lower or second chamber 14. A single action injection piston pump 25 is slidably mounted in the upper chamber while a single action withdrawal piston pump 26 is slidably mounted in the lower chamber 24. Both pumps include a piston rod 28, 29 respectively, slidably and sealingly extending through an apertured plate 30 secured to the housing wall and unitarily enclosing one end of the respective cylinders 22, 24. In the form shown, the cylinders 22, 24 share a common wall 31 and both cylinders open through said common wall 31 at a point adjacent the ends thereof opposite from the closure plate 30 into a passage 32 which in turn opens into the body cavity conduit through port member 20 and passage 21. Alternatively, the cylinders may open into a manifold which carries the port member 20. The upper or first cylinder is in communication wity the upper or first chamber 12, through a port 34 in the cylinder wall adjacent the sealing cap 30. Similarly, the lower or waste withdrawal cylinder 24 is in communication with the second or waste chamber 14 through a port 36 in the cylinder wall adjacent the cylinder end closure 30.

Figure 2:
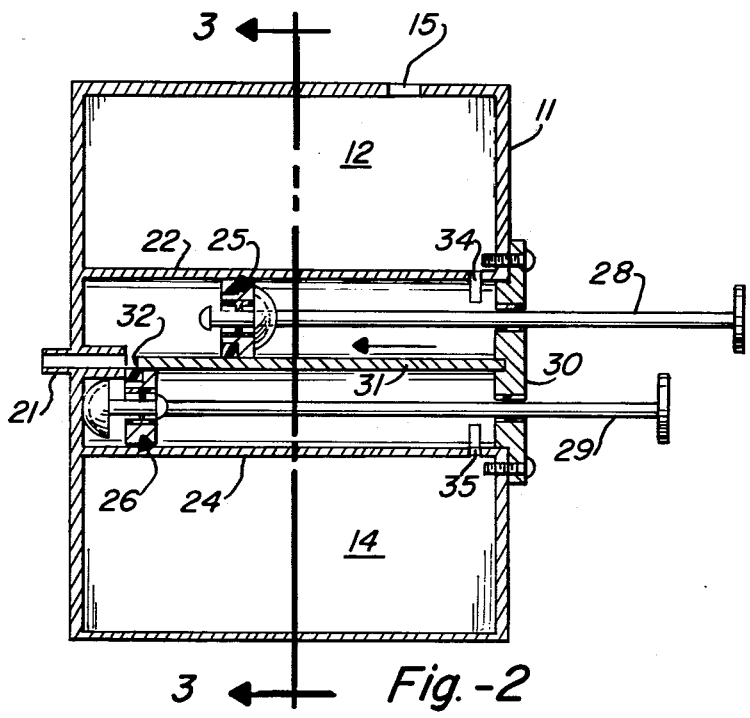
FIG. 2 is a section view taken substantially in the plane of line 2—2 on FIG. 1, and showing the device in irrigating solution injection configuration.
Figure 3:
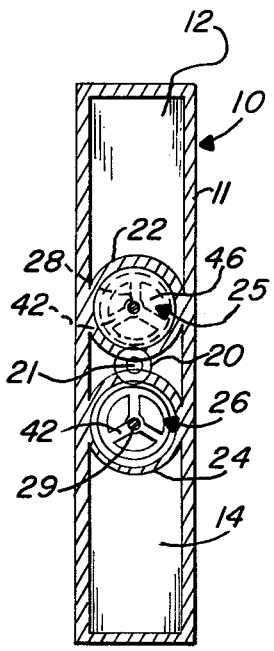
FIG. 3 is a section view taken substantially in the plane of line 3—3 on FIG. 2.

Pump pistons are operatively associated with each of the piston rods 28, 29 and are formed by a generally annular piston member 40 slidably mounted within the respective cylinder. Each piston member 40 includes a seal member or O-ring 41 in slidable and sealing engagement with the cylinder wall. The central portion of each annular piston member 40 is formed by a spider 42 including a central annular support sleeve 44 which slidably supports the piston rod and valve mechanism. Turning first to the upper pump, the piston rod 28 extends through the central aperture of the annular sleeve member 44 of the spider and is provided at its end with an enlarged knob or boss 45, the piston rod 28 is provided with a flexible circular sealing member of disc 46 having a diameter sufficient to seat and seal against the piston 40. When so seated, the circular sealing member 46 prevents the passage of liquid through the central spider portion of the piston. This construction provides a single action piston pump. Referring to the upper or injection pump, when the piston rod, as shown in FIG. 2, is pushed from right to left, a pumping force is exerted on liquid contained in the cylinder on the left hand or injection side of the piston 40. When the piston rod 28 is pulled from left to right, the sealing valve member 46 is pulled away from the piston 40, allowing passage of liquid through the central spider 42. Similarly, with respect to the lower pump, the piston rod 29 extends through the spider 42 of the piston 40 and is provided at its left hand or suction end with a flexible sealing disc 48. This disc 48, like the corresponding upper piston disc 46, is of a diameter sufficient to overlie the piston 40 to prevent the passage of liquid through the central spider 42. At the opposite side of the spider from the sealing disc 48, the piston rod 29 is provided with an enlarged boss or ring 49. In operation, by pulling on the piston rod 29, the sealing disc 48 engages the piston 40 to provide a suction as the piston is moved. When pushed in the opposite direction, the boss 49 engages the spider to move the piston while allowing for a free flow of liquid through the spider portion of the piston. As an alternative piston construction, any suitable one way valve mechanism such as a flexible disc or flap secured to the piston, may be utilized.

Figure 5:
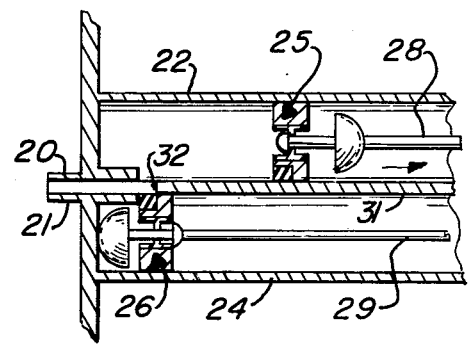
FIG. 5 is a section view similar to FIG. 4 but showing the irrigator in irrigating solution loading position.
Figure 4:
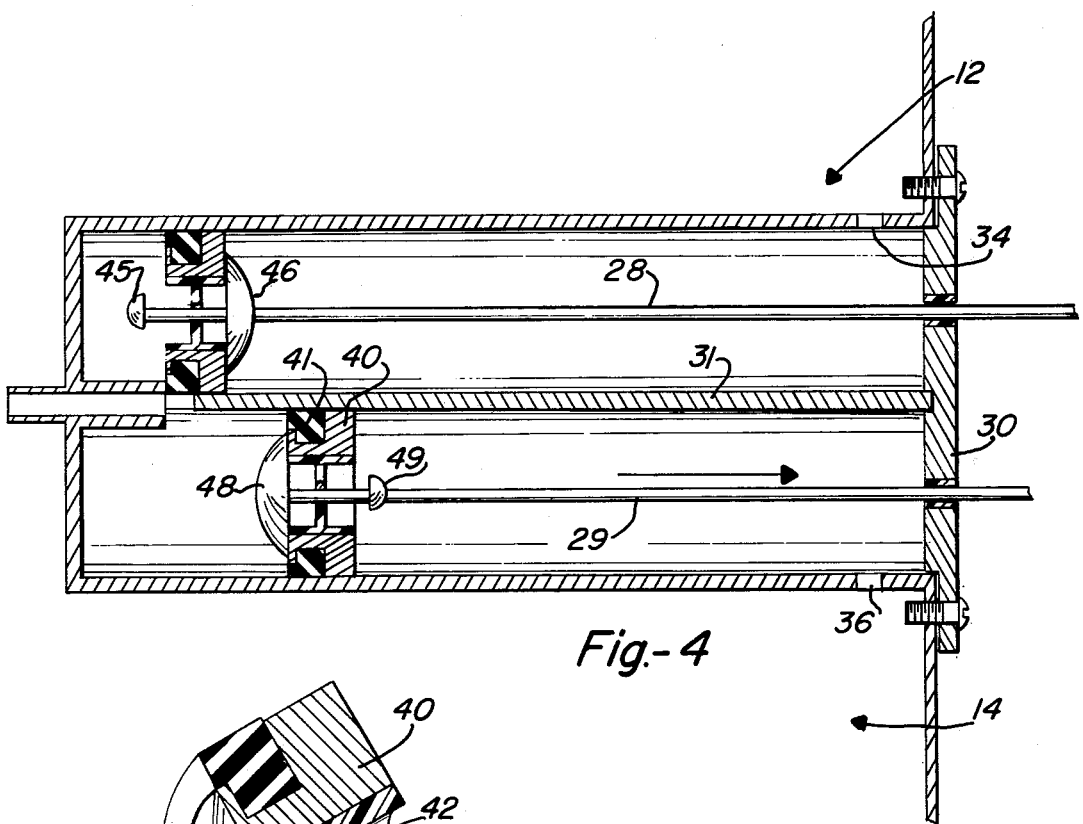
FIG. 4 is an enlarged fragmentary section view similar to FIG. 2 but showing the device in waste discharge configuration.
Figure 6:
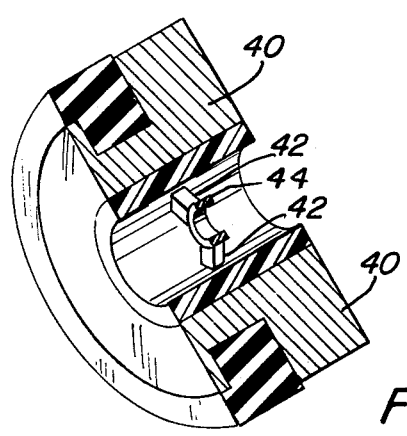
FIG. 6 is an enlarged section view taken through one of the pistons of the device shown in FIG. 4.

The irrigator device 10 embodying the present invention enables a user to inject a liquid or irrigating solution contained in the first or irrigating chamber into a body cavity, and to withdraw waste liquid from the body cavity. To irrigate a body cavity, utilizing the apparatus embodying the present invention, an irrigating solution is introduced into the first or upper chamber 12 through the inlet port 15. The unit 10 is connected to the body cavity through an appropriate flexible conduit (not shown) connected to the solution outlet 20 and outlet passage 21. The upper piston 25 is pulled from left to right, that is outwardly of the unit, to fill the portion of the cylinder in front of the piston with the irrigating solution. The solution flows through port 34 and through the piston spider as the piston rod is pulled outwardly in the direction of the arrow 50 in FIG. 5. During the filling of the injection pump 25, the withdrawal pump is positioned at its left most or closed position as shown in FIG. 5. To inject the solution into the body cavity, the user then pushes on the injection piston 25 to move it in the direction of arrow 51 in FIG. 2. During this motion, the valve seal member 46 seats against the piston and the piston forces the irrigating solution into the body cavity through the outlet port 32 and passage 21. After allowing the irrigating solution to remain in the body cavity for an appropriate period of time, the user then pulls outwardly on the discharge pump 26, in the direction of arrow 52 in FIG. 4. During this operation, the piston seal 48 seats against the piston 40 to create a suction which withdraws fluid from the body cavity into the lower or second cylinder 24. By reversing the direction of movement of the withdrawal pump, the lower piston seal 48 is opened and, as the piston moves forwardly, that is from right to left, waste fluids flow through the piston spider and drain through the discharge port 35 into the waste chamber 14. The operation may be repeated as many times as is desired, until the irrigating solution in the upper chamber 12 is exhausted.

While a certain illustrative irrigating device for irrigating internal body cavities has been shown in the drawings and described above in detail, it should be understood that there is no intention to limit the invention to the specific form disclosed. On the contrary, the intention is to cover all modifications, alternative constructions, equivalents and uses falling within the spirit and scope of the invention as expressed in the appended claims.

We claim as our invention:

1. An irrigator for use in irrigating internal body cavities, comprising a unitary housing defining a first chamber for holding a supply of an irrigating solution liquid for irrigating a body cavity and a second chamber for receiving and retaining waste liquid from the body cavity; a first single action pump having an intake stroke for receiving a measured quantity of liquid from the first chamber and an output stroke for pumping the liquid into the body cavity; and a second single action pump having an intake stroke for withdrawing waste liquid from the body cavity and an output stroke for discharging said waste liquid into said second chamber; said first and second pumps each having a port in communication with a single conduit connectable with the body cavity.

2. An irrigator as defined in claim 1 wherein said first and second pumps are piston pumps.

3. An irrigator as defined in claim 2 wherein each of said piston pumps includes a one-way diaphragm valve.

4. An irrigator as defined in claim 1 wherein said first pump defines a portion of the wall of said first chamber and said second pump defines a portion of the wall of said second chamber, said first pump being in communication with said first chamber and said second pump being in communication with said second chamber.

5. An irrigator as defined in claim 4 wherein said pumps are integrally juxtaposed and include a common port respectively communicating with a single conduit connectable with the body cavity.

6. An irrigator as defined in claim 1 wherein said first pump port is closed when said first pump is at the end of its output stroke and said second pump port is closed when said second pump is at the beginning of its intake stroke.

7. An irrigator as defined in claim 6 wherein the strokes of said first and second pumps are coordinated so that said second pump is at the beginning of its intake stroke during the operation of said first pump in receiving a measured quantity of liquid from the first chamber and pumping the same into the body cavity, and said first pump is at the end of its output stroke during operation of said second pump for withdrawing waste liquid from the body cavity and discharging said waste liquid into said second chamber, thereby preventing cross-flow of liquids between said pumps and chambers.

* * * * *